(12) United States Patent
Walsh et al.

(10) Patent No.: US 11,529,143 B2
(45) Date of Patent: Dec. 20, 2022

(54) FLOW CONTROL VALVE

(71) Applicant: Boston Scientific Scimed, Inc., Maple Grove, MN (US)

(72) Inventors: Michael Walsh, Galway (IE); Darren Curran, Galway (IE); Otto Van Der Kooij, Roscommon (IE); Daniel Tuck, Galway (IE); Javier Palomar-Moreno, Galway (IE); Jeff Gray, Sudbury, MA (US); Martyn Folan, Galway (IE); Emma J. Mooney, Galway (IE); Enda Hannon, Galway (IE)

(73) Assignee: BOSTON SCIENTIFIC, SCIMED, INC., Maple Grove, MN (US)

( * ) Notice: Subject to any disclaimer, the term of this patent is extended or adjusted under 35 U.S.C. 154(b) by 658 days.

(21) Appl. No.: 16/361,695

(22) Filed: Mar. 22, 2019

(65) Prior Publication Data

US 2019/0298364 A1 Oct. 3, 2019

Related U.S. Application Data

(60) Provisional application No. 62/650,068, filed on Mar. 29, 2018.

(51) Int. Cl.
*A61B 17/12* (2006.01)
*A61M 31/00* (2006.01)
(Continued)

(52) U.S. Cl.
CPC ...... *A61B 17/1114* (2013.01); *A61B 17/1204* (2013.01); *A61B 17/12168* (2013.01); *A61M 31/002* (2013.01); *A61B 2017/00893* (2013.01); *A61B 2017/1139* (2013.01); *A61B 2017/1205* (2013.01); *A61M 25/0023* (2013.01); *A61M 27/002* (2013.01); *A61M 2025/0024* (2013.01)

(58) Field of Classification Search
CPC ........... A61F 2230/0095; A61F 2/90; A61F 2230/0069; A61F 2/915; A61F 5/0079; A61F 2/00; A61F 2/0108; A61F 2/0105; A61F 2002/91533; A61F 2250/0018; A61M 2205/04; A61M 2025/0024; (Continued)

(56) References Cited

U.S. PATENT DOCUMENTS 5,755,778 A * 5/1998 Kleshinski ............... A61F 2/91
623/1.13
8,323,350 B2 12/2012 Nissl
(Continued)

FOREIGN PATENT DOCUMENTS

WO 2016192781 A1 12/2016

OTHER PUBLICATIONS

International Search Report and Written Opinion for International application No. PCT/US2019/023592, dated Jun. 28, 2019, 11 pages.
(Continued)

*Primary Examiner* — Kai H Weng
*Assistant Examiner* — Seth Han
(74) *Attorney, Agent, or Firm* — Seager, Tufte & Wickhem, LLP

(57) ABSTRACT

The present disclosure relates generally to the field of medical devices and establishing fluid communication between body lumens. In particular, the present disclosure relates to devices and methods for establishing a controlled flow or access passage between body lumens.

8 Claims, 12 Drawing Sheets

(51) Int. Cl.
*A61M 25/00* (2006.01)
*A61B 17/00* (2006.01)
*A61M 27/00* (2006.01)
*A61B 17/11* (2006.01)

(58) Field of Classification Search
CPC ........ A61M 2024/0025; A61M 27/002; A61M 25/0023; A61M 31/002; A61B 17/12022; A61B 17/12036; A61B 17/12031; A61B 17/12027; A61B 17/12045; A61B 17/1204; A61B 17/12109; A61B 17/12172; A61B 17/1114; A61B 17/12168; A61B 2017/00893
USPC .......................................................... 604/8
See application file for complete search history.

(56) References Cited

U.S. PATENT DOCUMENTS

| | | | |
|---|---|---|---|
| 8,764,772 B2 * | 7/2014 | Tekulve | A61B 17/12177 606/151 |
| 9,044,300 B2 | 6/2015 | Belhe et al. | |
| 10,420,665 B2 | 9/2019 | Sharma et al. | |
| 2009/0093837 A1 | 4/2009 | Dillon | |
| 2009/0240324 A1 * | 9/2009 | Smith | A61L 31/088 623/1.42 |
| 2013/0030351 A1 | 1/2013 | Belhe et al. | |
| 2015/0374383 A1 | 12/2015 | Bodewadt et al. | |
| 2016/0256169 A1 | 9/2016 | Ben-Muvhar et al. | |
| 2017/0119520 A1 | 5/2017 | Hingston et al. | |
| 2017/0224323 A1 | 8/2017 | Rowe et al. | |
| 2018/0021156 A1 | 1/2018 | Ben-Muvhar et al. | |

OTHER PUBLICATIONS

Yonemura, Y., et al., "Recent advances in the treatment of peritoneal dissemination of gastrointestinal cancers by nucleoside antimetabolites", Cancer Sci. 98(1):11-18 (2007).

Author unknown, "Counting Cells for Immunology Using Cellometer Auto T4 Cell Counter" Nexcelom Bioscience [online] date unknown [retrieved on Aug. 21, 20199], Retrieved from Internet URL: http://www.nexcelom.com/Literature/App%20Note%2006005%20Immunology.pdf, 3 pages.

* cited by examiner

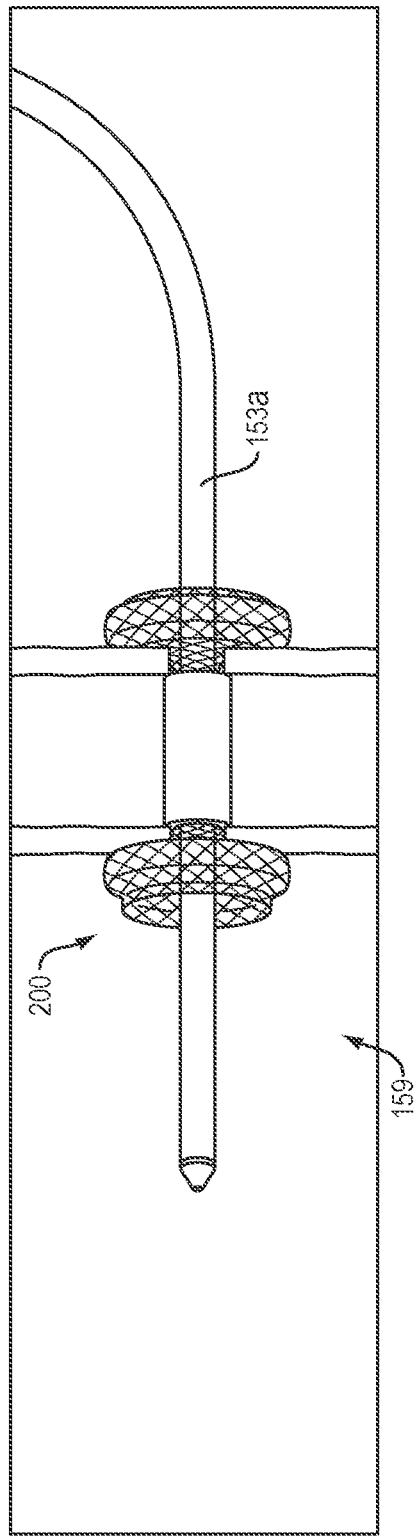
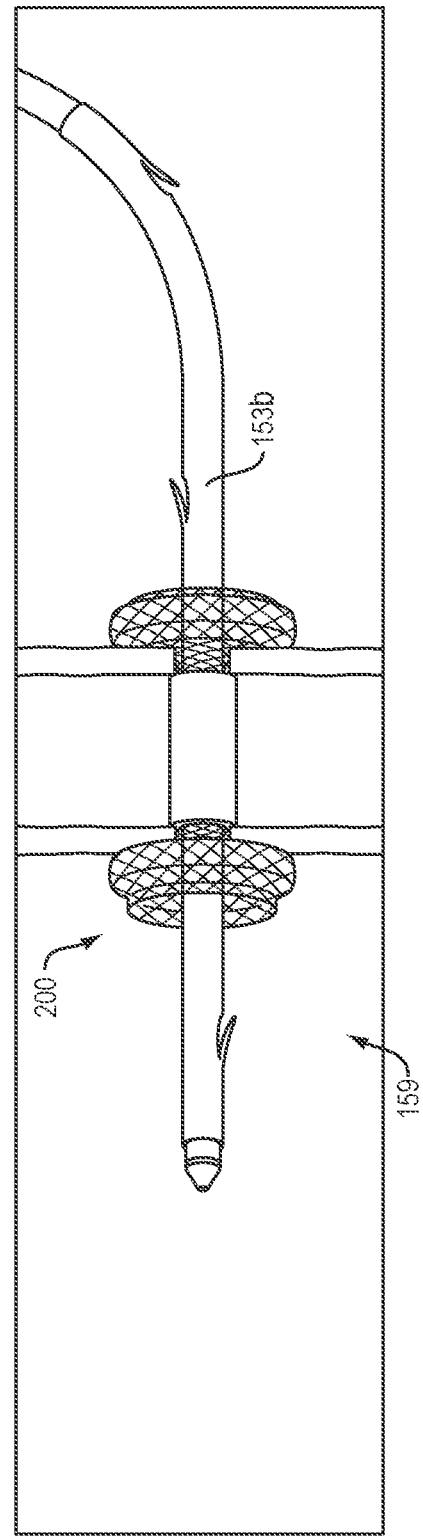

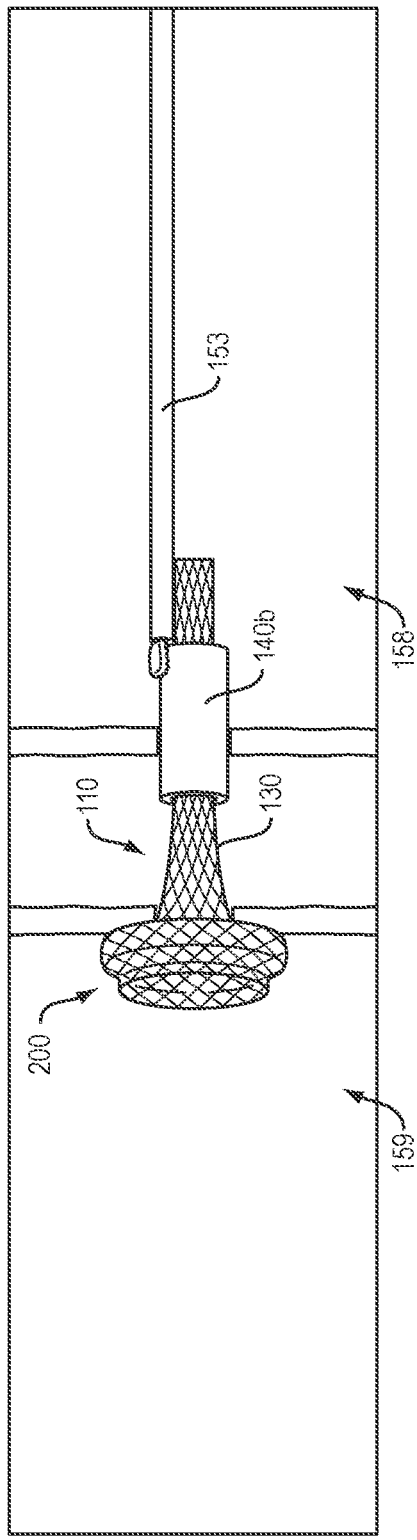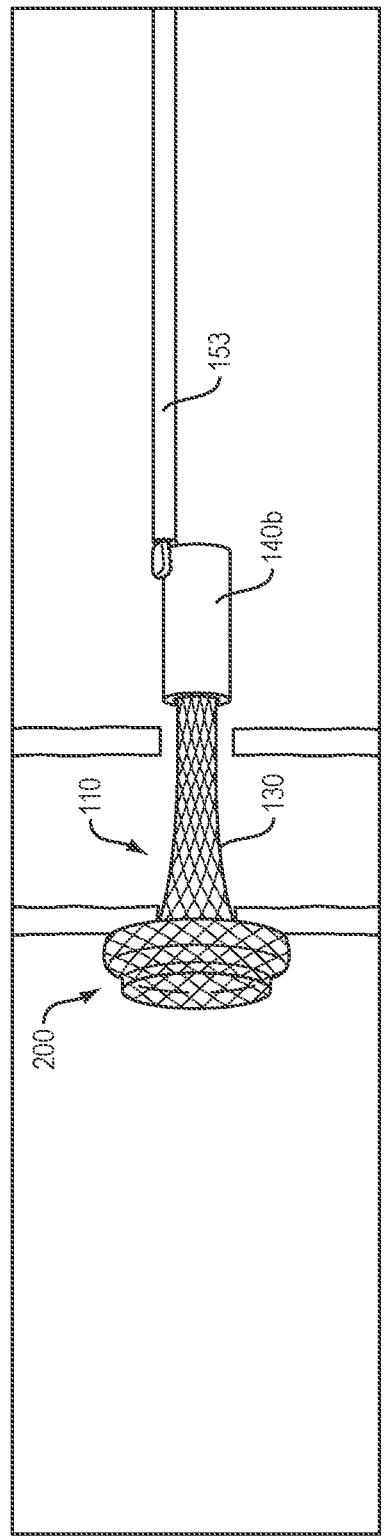

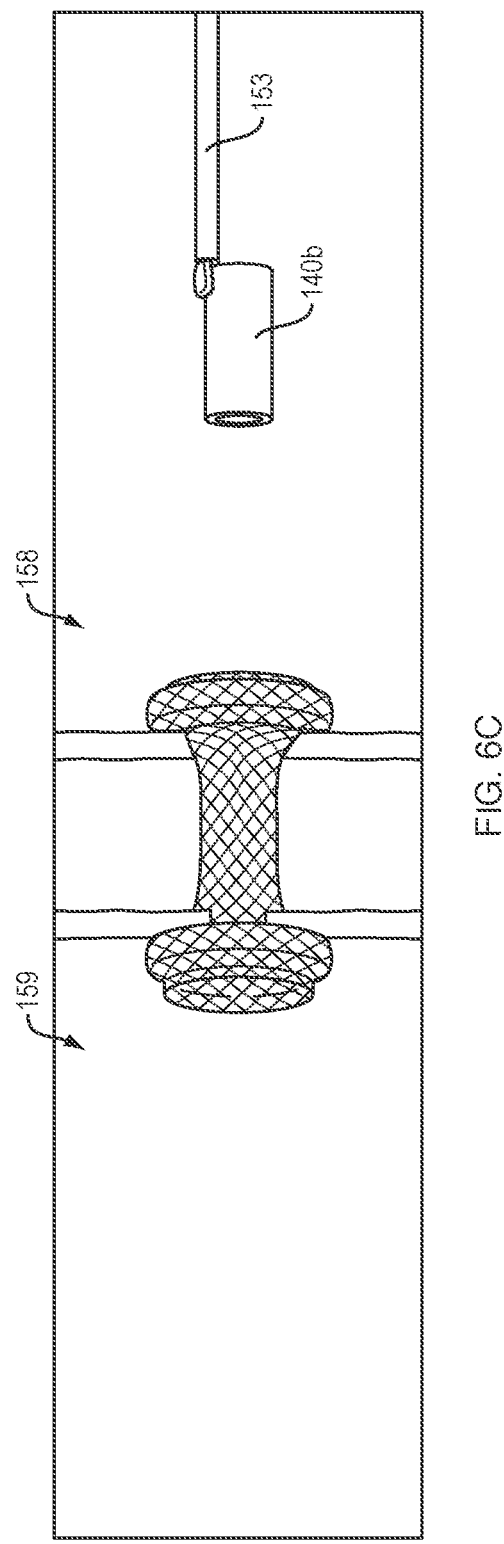

FLOW CONTROL VALVE

CROSS REFERENCE TO RELATED APPLICATIONS

This application claims the benefit of priority under 35 U.S.C. § 119 to U.S. Provisional Patent Application Ser. No. 62/650,068, filed on Mar. 29, 2018, which is incorporated by reference in its entirety for all purposes.

FIELD

The present disclosure relates generally to the field of medical devices and establishing fluid communication between body lumens. In particular, the present disclosure relates to devices and methods for establishing a controlled flow or access passage between body lumens.

BACKGROUND

The desire to establish access between two body lumens to create fluid communication from one to the other is present under various circumstances and conditions. A variety of medical devices (e.g., anastomotic devices, drainage stents, etc.) are able to establish open flow or access passages between body lumens. For example, an anastomotic or drainage device which facilitates transgastric or transduodenal drainage of a symptomatic pancreatic pseudocyst adherent to the gastric or bowel wall may remain implanted for up to 60 days. The open access path provided by the device may allow the continued flow of fluid and/or debris from the pancreatic pseudocyst into the stomach or duodenum. Resolution of the pancreatic pseudocyst may be further enhanced by the flow of acidic stomach fluids into the pseudocyst, which neutralize the alkalinity and increase the viscosity of the fluid and/or debris. While continual unidirectional flow or bi-directional flow through the medical device may be advantageous in certain circumstances, various medical conditions require controlled periodic or intermittent drainage and/or access to a body lumen or organ.

A variety of advantageous medical outcomes may be realized by the devices and/or methods of the present disclosure which allow, for example, infusion and/or drainage of body lumens or organs in a controlled manner for a period of time.

SUMMARY

In one aspect, the present disclosure relates to a medical device comprising an elongate tubular body, which may include a proximal portion, a distal portion and a length therebetween. The elongate tubular body may define a lumen along the length. The elongate tubular body may have an unexpanded configuration, and an expanded configuration wherein the proximal portion may expand into a proximal retention member, and the distal portion may expand into a distal retention member leaving a length of a saddle region (e.g., a cylindrical saddle region) extending therebetween. A flexible member may be disposed around the saddle region and along at least a portion of the length of the saddle region. The flexible member may be configured to constrict at least a portion of the length of the saddle region. The flexible member may be removably disposed around the saddle region. The flexible member may be permanently disposed around the saddle region. The flexible member may include a sheath disposed around the saddle region and along a portion of all or a substantial portion of the length of the saddle region. The flexible member may include a collar disposed around the saddle and along a portion of the length of the saddle region. The medical device may include two (or more) flexible collars spaced apart from each other and disposed around the saddle region. A portion of the length of the saddle region between the two flexible collars may define a reservoir. The flexible member may define a lumen. The flexible member may be configured to move from a first non-expanded configuration to a second expanded configuration. An inner dimension of the lumen of the flexible member in the first non-expanded configuration may be less than an inner dimension of the lumen of the flexible member in the second expanded configuration. The lumen of the constricted portion of the length of the saddle region may be completely closed when the flexible member is in the first non-expanded configuration. The lumen of the constricted portion of the length of the saddle region may be partially closed when the flexible member is in the first non-expanded configuration. A therapeutic agent may be disposed within the reservoir. The therapeutic agent may flow from the reservoir through the proximal retention member. The therapeutic agent may flow from the reservoir through the distal retention member. A surface of the proximal retention member may be configured to contact an inner surface of a tissue wall of a first body lumen, and a surface of the distal retention member may be configured to contact an inner surface of a tissue wall of a second body lumen. In addition, or alternatively, a surface of the proximal retention member may be configured to contact an inner surface of a tissue wall of a first body lumen, and a surface of the distal retention member may be configured to contact an outer surface of the tissue wall of the first body lumen. The distal retention member, proximal retention member and/or saddle region may be covered. The flexible member and the constricted portion of the length of the saddle region may be configured to move from a first diameter configuration to an expanded second diameter configuration in response to a threshold level of force, including, for example, the force exerted by a second medical device inserted into the lumen of the medical device. A second medical device may extend through the lumen of the saddle region. The second medical device may deliver a therapeutic agent into the second body lumen. The second medical device may be configured to suction fluid or debris from within the second body lumen. The second medical device may be a drainage device.

In another aspect, the present disclosure relates to a medical device comprising an elongate tubular body, which may include a proximal portion, a distal portion, and a length therebetween. The elongate tubular body may define a lumen along the length. The elongate tubular body may have an unexpanded configuration, and an expanded configuration wherein the proximal portion may expand into a proximal retention member, and the distal portion may expand into a distal retention member leaving a length of a saddle region (e.g., a cylindrical saddle region) extending therebetween. A flexible collar may be disposed around the saddle region along the length of a portion of the saddle region. The flexible collar may be configured to constrict at least a portion of the length of the saddle region. The flexible collar may be removably disposed around the saddle region. The flexible collar may be permanently disposed around the saddle region. The flexible collar may define a lumen. The flexible collar may be configured to move from a first non-expanded configuration to a second expanded configuration. An inner dimension of the lumen of the flexible collar in the first non-expanded configuration may be less than an inner dimension of the lumen of the flexible collar in the second expanded configuration. The lumen of the constricted portion of the length of the saddle region may be completely closed when the flexible collar is in the first non-expanded configuration. The lumen of the constricted portion of the length of the saddle region may be partially closed when the flexible collar is in the first non-expanded configuration. A surface of the proximal retention member may be configured to contact an inner surface of a tissue wall of a first body lumen, and a surface of the distal retention member may be configured to contact an inner surface of a tissue wall of a second body lumen. In addition, or alternatively, a surface of the proximal retention member may be configured to contact an inner surface of a tissue wall of a first body lumen, and a surface of the distal retention member may be configured to contact an outer surface of the tissue wall of the first body lumen. The distal retention member, proximal retention member and/or saddle region may be covered. The flexible collar and the constricted portion of the length of the saddle region may be configured to move from a first diameter configuration to an expanded second expanded diameter configuration in response to a threshold level of force, including, for example, the force exerted by a second medical device inserted into the lumen of the medical device. A second medical device may extend through the lumen of the saddle region. The second medical device may deliver a therapeutic agent into the second body lumen. The second medical device may be configured to suction fluid or debris from within the second body lumen. The second medical device may be a drainage device. The second medical device may be a valve.

In yet another aspect, the present disclosure relates to a medical device comprising an elongate tubular body, which may include a proximal portion, a distal portion, and a length therebetween. The elongate tubular body may define a lumen along the length. The elongate tubular body may have an unexpanded configuration, and an expanded configuration wherein the proximal portion may expand into a proximal retention member, and the distal portion may expand into a distal retention member leaving a length of a saddle region (e.g., a cylindrical saddle region) extending therebetween. Two (or more) flexible collars may be disposed around the saddle region along separate portions of the length of the saddle region. Each of the flexible collars may be configured to constrict at least a portion of the saddle region. A portion of the saddle region between the flexible collars may define a reservoir. The flexible collars may be removably disposed around the saddle region. The flexible collars may be permanently disposed around the saddle region. Each flexible collar may define a lumen. Each flexible collar may be configured to move from a first non-expanded configuration to a second expanded configuration. An inner dimension of the lumen of each flexible collar in the first non-expanded configuration may be less than an inner dimension of the lumen of each flexible collar in the second expanded configuration. The lumen of the constricted portion of the length of the saddle region may be completely closed when the flexible collars are in the first non-expanded configuration. The lumen of the constricted portion of the length of the saddle region may be partially closed when the flexible collars are in the first non-expanded configuration. A therapeutic agent may be disposed within the reservoir. The therapeutic agent may flow from the reservoir through the proximal retention member. The therapeutic agent may flow from the reservoir through the distal retention member. A surface of the proximal retention member may be configured to contact an inner surface of a tissue wall of a first body lumen, and a surface of the distal retention member may be configured to contact an inner surface of a tissue wall of a second body lumen. In addition, or alternatively, a surface of the proximal retention member may be configured to contact an inner surface of a tissue wall of a first body lumen, and a surface of the distal retention member may be configured to contact an outer surface of the tissue wall of the first body lumen. The distal retention member, proximal retention member and/or saddle region may be covered. The flexible collars and the constricted portion of the length of the saddle region may be configured to move from a first diameter configuration to a second expanded diameter configuration in response to a threshold level of force, including, for example, the force exerted by a second medical device inserted into the lumen of the medical device. A second medical device may extend through the lumen of the saddle region. The second medical device may deliver a therapeutic agent into the second body lumen. The second medical device may be configured to suction fluid or debris from within the second body lumen. The second medical device may be a drainage device. The second medical device may be a valve.

In yet another aspect, the present disclosure relates to a medical device comprising an elongate tubular body, which may include a proximal portion, a distal portion, and a length therebetween. The elongate tubular body may define a lumen along the length. The elongate tubular body may have an unexpanded configuration, and an expanded configuration wherein the proximal portion may expand into a proximal retention member, the distal portion may expand into a distal retention member leaving a saddle region (e.g., a cylindrical saddle region) extending therebetween. A flexible sheath may be disposed around the saddle region and along all or a substantial portion of the length of the saddle region. The flexible sheath may be configured to constrict at least a portion of the saddle region. The flexible sheath may be removably disposed around the saddle region. The flexible sheath may be permanently disposed around the saddle region. The flexible sheath may define a lumen. The flexible sheath may be configured to move from a first non-expanded configuration to a second expanded configuration. An inner dimension of the lumen of the flexible sheath in the first non-expanded configuration may be less than an inner dimension of the lumen of the flexible sheath in the second expanded configuration. The lumen of the constricted portion of the length of the saddle region may be completely closed when the flexible sheath is in the first non-expanded configuration. The lumen of the constricted portion of the length of the saddle region may be partially closed when the flexible sheath is in the first non-expanded configuration. A surface of the proximal retention member may be configured to contact an inner surface of a tissue wall of a first body lumen, and a surface of the distal retention member may be configured to contact an inner surface of a tissue wall of a second body lumen. In addition, or alternatively, a surface of the proximal retention member may be configured to contact an inner surface of a tissue wall of a first body lumen, and a surface of the distal retention member may be configured to contact an outer surface of the tissue wall of the first body lumen. The distal retention member, proximal retention member and/or saddle region may be covered. The flexible sheath and the constricted portion of the saddle region may be configured to move from a first diameter configuration to an expanded second diameter configuration in response to a threshold level of force, including, for example, the force exerted by a second medical device inserted into the lumen of the medical device. A second medical device may extend through the lumen of the saddle region. The second medical device may deliver a therapeutic agent into the second body lumen. The second medical device may be configured to suction fluid or debris from within the second body lumen. The second medical device may be a drainage device. The second medical device may be a valve.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A-5B provide side perspective views of a medical device, extending through a medical device according to one embodiment of the present disclosure.

FIGS. 6A-6C provide side perspective views of a medical device, according to one embodiment of the present disclosure.

DETAILED DESCRIPTION

Figure 1B:
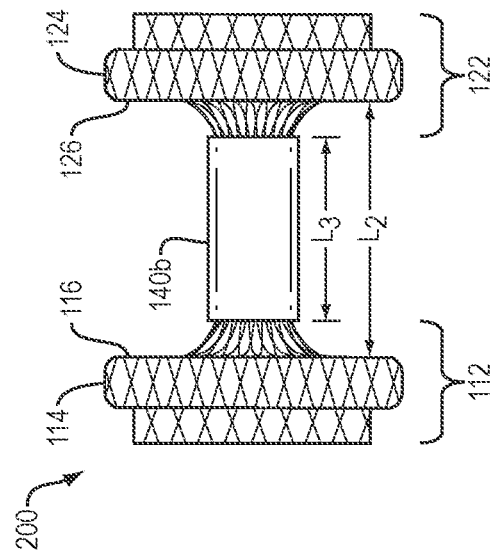
FIGS. 1A-1D provide side (FIGS. 1A-1B) and front (FIGS. 1C-1D) perspective views of a medical device, according to one embodiment of the present disclosure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices (e.g., anastomotic devices, drainage stents, etc.) and systems to establish and/or maintain a controlled periodic or intermittent flow or access passage from or between the stomach or duodenal wall into the peritoneal cavity, it should be appreciated that such medical devices may be used in a variety of medical procedures, including natural orifice transluminal endoscopic surgery (NOTES) procedures, (e.g., external biliary drain conversion, enteroenterostomy, gastrojejumostomy, gastroduodenostomy and gastroileostomy, transcolonic procedures, transgastric procedures, transtracheal procedures, transvaginal procedures, cholelithiasis procedures, choledocholiathiasis procedures, etc.) to establish and/or maintain a controlled periodic or intermittent flow or access passage from or between a variety of body organs, lumens, ducts, vessels, fistulas, cysts and/or spaces (e.g., the dermis, stomach, duodenum, jejunum, small intestine, gallbladder, kidneys, pancreas, biliary/pancreatic trees, bladder, ureter, abscesses, walled-off pancreatic necrosis (WOPN), bile ducts, etc.). The devices can be inserted via different access points and approaches, e.g., percutaneously, endoscopically, laparoscopically or some combination thereof. The medical devices disclosed herein are self-expanding, but in other embodiments the medical devices may be expandable by other means, including, e.g., a balloon catheter. Moreover, such medical devices are not limited to drainage, but may facilitate controlled access to organs, vessels or body lumens for other purposes, such as delivery of therapeutic agents and/or creating a path to divert or bypass fluids or solids from one location to another, removing obstructions and/or non-invasive or minimally invasive manipulation of tissues.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In one embodiment, the present disclosure relates to a medical device (e.g., anastomotic device, drainage stent, etc.) which may allow an efficient mechanism for controlled periodic access to a body lumen or organ to facilitate direct endoscopic delivery of Advanced Therapy Medicinal Products (ATMP's), e.g., immune check-point inhibitors, therapeutic agents, drugs, cellular therapy solutions, etc., for maximal therapeutic effect and minimal patient discomfort. For example, a medical device of the present disclosure may support controlled repeated/intermittent endoscopic delivery of immune boosting therapeutic fluids through the stomach or duodenal wall into a body cavity comprising or adjacent to a diseased organ or tissue.

Figure 1D:
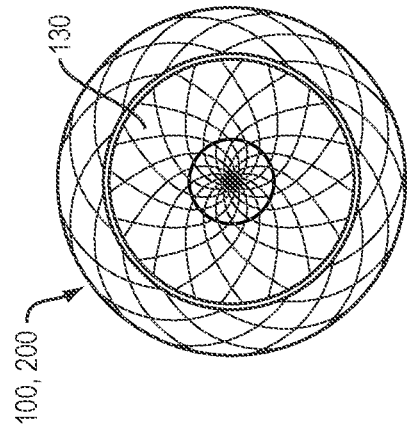
Figure 1A:
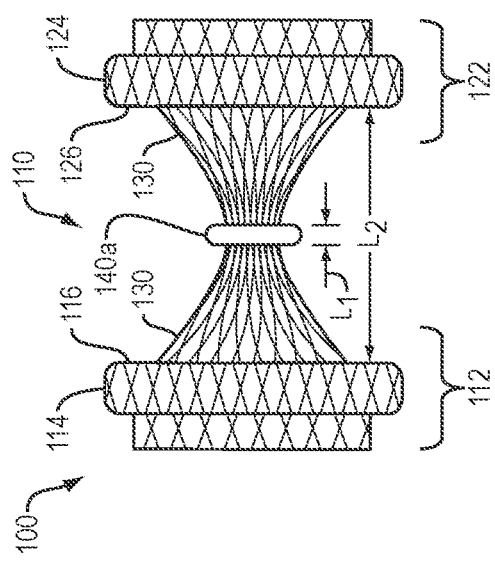

Referring to FIG. 1A, in one embodiment, a medical device 100 of the present disclosure may include an elongate tubular body 110 forming a lumen and comprising a proximal portion 112, a distal portion 122, a length and a diameter. The elongate tubular body 110 may include an unexpanded configuration (e.g., constrained, undeployed or delivery configuration; not shown), and an expanded configuration (e.g., unconstrained, delivered or deployed configuration) where the proximal portion 112 radially expands into a proximal retention member 114, and the distal portion 122 radially expands into a distal retention member 124, leaving a length of a saddle region 130 (e.g., cylindrical saddle region) extending therebetween. The proximal and distal retention members 114, 124 may extend radially from (e.g., perpendicular to a circumference of) the elongate tubular body 110 to define respective surfaces 116, 126. In various embodiments, a flexible member 140*a* may be disposed around (e.g., around a full circumference) the saddle region and along at least a portion of the length saddle region 130. The flexible member 140*a* may be formed from a variety of compliant or semi-compliant materials (e.g., rubber, silicone, elastomeric materials, polymeric materials, etc.) configured to decrease a diameter of (e.g., constrict, collapse, narrow, etc.) the lumen of the saddle region 130. Still referring to FIG. 1A, in one embodiment, the flexible member 140*a* may include a ring or collar, e.g., having a length $L_1$ less than a length $L_2$ of the saddle region 130, such that only a portion of the lumen along the length of the saddle region 130 is constricted. Although the flexible member 140a (e.g., ring/collar) is positioned at an approximate mid-point of the saddle region 130, in various embodiments, the flexible member 140a may be positioned along any portion of the length of the saddle region 130 between the proximal and distal retention members 114, 124. In addition, or alternatively, as discussed in greater detail below (e.g., FIGS. 3A-3C), more than one flexible member 140a, (e.g., two or more rings/collars) may be disposed around the saddle region 130 and spaced apart from each other. Referring to FIG. 1B, in one embodiment, the flexible member 140b may include a sheath or tube, e.g., having a length $L_3$ equal to, or slightly less than, the length $L_2$ of the saddle region 130, such that all or a substantial portion of the length of the lumen of the saddle region 130 is constricted.

Figure 1C:
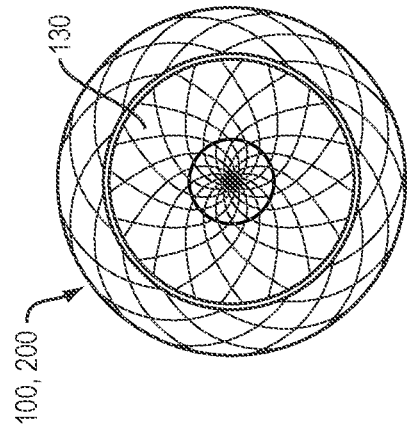

Referring to the cross-section view of FIG. 1C, in various embodiments, the flexible member 140a, 140b may include a relaxed configuration which defines a lumen 141 with a first inner dimension $d_1$ configured to completely close the lumen along at least a portion of the length of the saddle region 130, thereby eliminating/preventing the flow of fluids and/or materials therethrough. For example, FIG. 1D provides a front perspective view of the medical device 100, 200 of FIG. 1A or 1B, with the flexible member (not shown) in a relaxed configuration such that substantially no opening or access passage extends through the lumen of the saddle region 130.

Figure 2B:
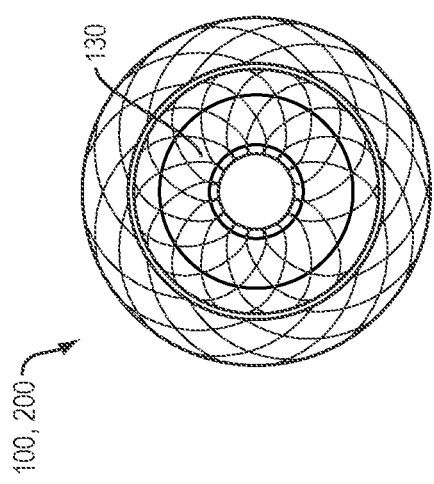
FIGS. 2A-2B provide front perspective views of a medical device, according to one embodiment of the present disclosure.
Figure 2A:
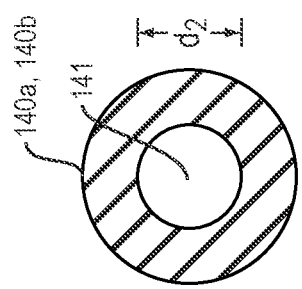

Referring to the cross-sectional view of FIG. 2A, in various other embodiments, the flexible member 140a, 140b may include a relaxed configuration which defines a lumen 141 with a first inner dimension $d_2$ configured to partially close the lumen along at least a portion of the length of the saddle region 130, thereby limiting or slowing (but not preventing) the flow of fluids and/or materials therethrough. For example, FIG. 2B provides a front perspective view of the medical device 100, 200 of FIG. 1A or 1B, with the flexible member (not shown) in a relaxed configuration such that a narrowed or constricted opening or access passage extends through the lumen of the saddle region 130.

By way of non-limiting example, depending on the flow and/or access requirements of a specific medical procedure, the first inner dimension $d_2$ of the lumen 141 of the flexible member 140a, 140b may constrict or narrow the lumen along at least a portion of the length of the saddle region 130 by, e.g., at least 90 percent, at least 80 percent, at least 70 percent, at least 60 percent, at least 50 percent, at least 40 percent, at least 30 percent, at least 20 percent or at least 10 percent.

In various embodiments, the flexible member 140a, 140b may be permanently attached to, or integrally formed with, the woven or braided filament of the elongate tubular body 110, e.g., disposed around the saddle region and along at least a portion of the elongate tubular body which forms the saddle region 130, using a suitable glue, adhesive, resin, solder or other bonding techniques, as are commonly known in the art. In various other embodiments, the flexible member may be removably attached, e.g., via a friction or interference fit, to the elongate tubular body (e.g., FIGS. 6A-6C).

Figure 3A:
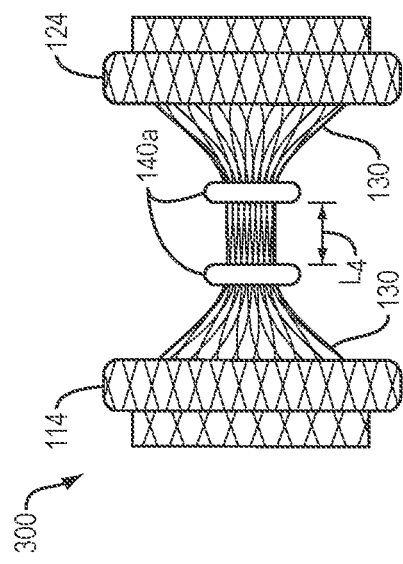
FIGS. 3A-3C provide side perspective views of a medical device, according to one embodiment of the present disclosure.

Referring to FIG. 3A, in one embodiment, a medical device 300 of the present disclosure may include the identical features of the medical device 100, with two flexible members 140a, e.g., rings/collars, spaced apart from each other and disposed around the saddle region 130 and separated by a length $L_4$. In various embodiments, the rings/collars 140a may including an inner dimension $d_1$ which completely or partially constricts/closes the lumen of the saddle region 130, thereby defining a reservoir 146 between the rings/collars. Referring to FIG. 3B, in one embodiment, the non-constricted portion of the saddle region 130 which defines the reservoir 146 may be filled, loaded or pre-loaded with a therapeutic agent (e.g., using a syringe, etc.) such that the therapeutic agent is maintained within the reservoir 146 under a predetermined level of pressure. In various embodiments, the pressure exerted by the therapeutic agent loaded within the reservoir 146 may provide controlled delivery of the therapeutic agent through one (or both) of the rings/collars into a respective body lumen. By way of non-limiting example, the therapeutic agent may be delivered as a controlled drip or flow over the course of minutes, hours, days and/or months.

In one embodiment, the constrictive force exerted by each of the rings/collars 140a disposed around and along a portion of the saddle region 130 may be substantially identical (FIGS. 3A-3B). Alternatively, in one embodiment, the constrictive force of the rings/collars 140a may be different, e.g., by varying the shape, composition, thickness and/or durometer value of the flexible members, such that flow of the therapeutic agent from the reservoir 146 occurs in one direction.

Figure 3C:
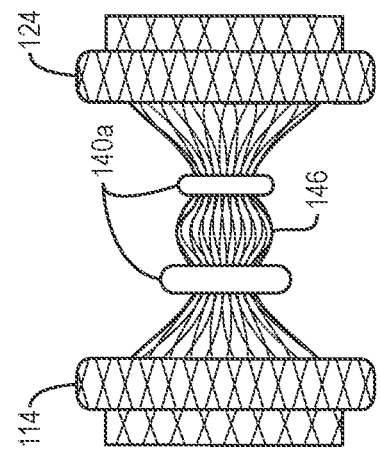
Figure 3B:
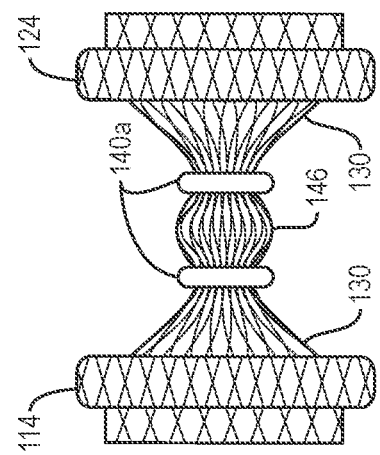

For example, referring to FIG. 3C, the constrictive force of the ring/collar 140a positioned adjacent to the proximal retention member 114 may be greater than the constrictive force of the ring/collar 140a positioned adjacent to the distal retention member 124, such that the therapeutic agent flows from the reservoir 146 through the distal retention member 124 and, e.g., into a second body lumen. In addition, or alternatively, the ring/collar 140a positioned adjacent to the proximal retention member 114 may include an inner dimension $d_1$ that completely constricts/closes the lumen of the saddle region 130, and the ring/collar 140a positioned adjacent to the distal retention member 124 may include a lumen 141 with an inner dimension $d_2$ that does not completely close the lumen of the saddle region, thereby providing controlled release of the therapeutic agent from the reservoir 146 through the distal retention member 124. As discussed above, the inner dimension $d_2$ of the lumen 141 of the distal-most ring/collar may be varied as necessary depending on the required release profile of the therapeutic agent from the reservoir 146.

In various other embodiments, the constrictive force of the rings/collars 140a may be reversed, e.g., such that the constrictive force of the ring/collar adjacent to the distal retention 124 member is greater than the constrictive force of the ring/collar adjacent to the proximal retention member 114, thereby supporting flow of the therapeutic agent from the reservoir 146 through the proximal retention member 114 and, e.g., into a first body lumen. Alternatively, in one embodiment, the direction of flow from the reservoir 146 may be determined by switching the relative locations of the proximal and distal flanges 114, 124 within the patient. For example, the medical device 300 may be positioned within a patient such that the proximal retention member 114 is placed in contact with the tissue wall of the second body lumen, and the distal retention member 124 is placed in contact with the tissue wall of first body lumen to effectuate the same purpose.

In various embodiments, the surface 116 of the proximal retention member 114 may atraumatically engage a (e.g., inner) tissue wall of a first body lumen, and the surface 126 of the distal retention member 124 may atraumatically engage a (e.g., inner) tissue wall of a second (e.g., adjacent or apposed) body lumen to prevent or limit movement/ migration of the deployed medical device 100, 200, 300 within or between the first and second body lumens. Alternatively, in one embodiment, the respective surfaces 116, 126 of the proximal and distal retention members 114, 124 may atraumatically engage opposite sides of a single tissue wall to prevent or limit movement/migration of the deployed medical device. For example, a medical device 100, 200, 300 of the present disclosure may be configured to extend through the wall of body lumen or organ (e.g., the stomach) to that the pleural space outside the stomach may be accessed by a medical device extending from inside the body lumen through the lumen of the medical device.

Figure 4A:
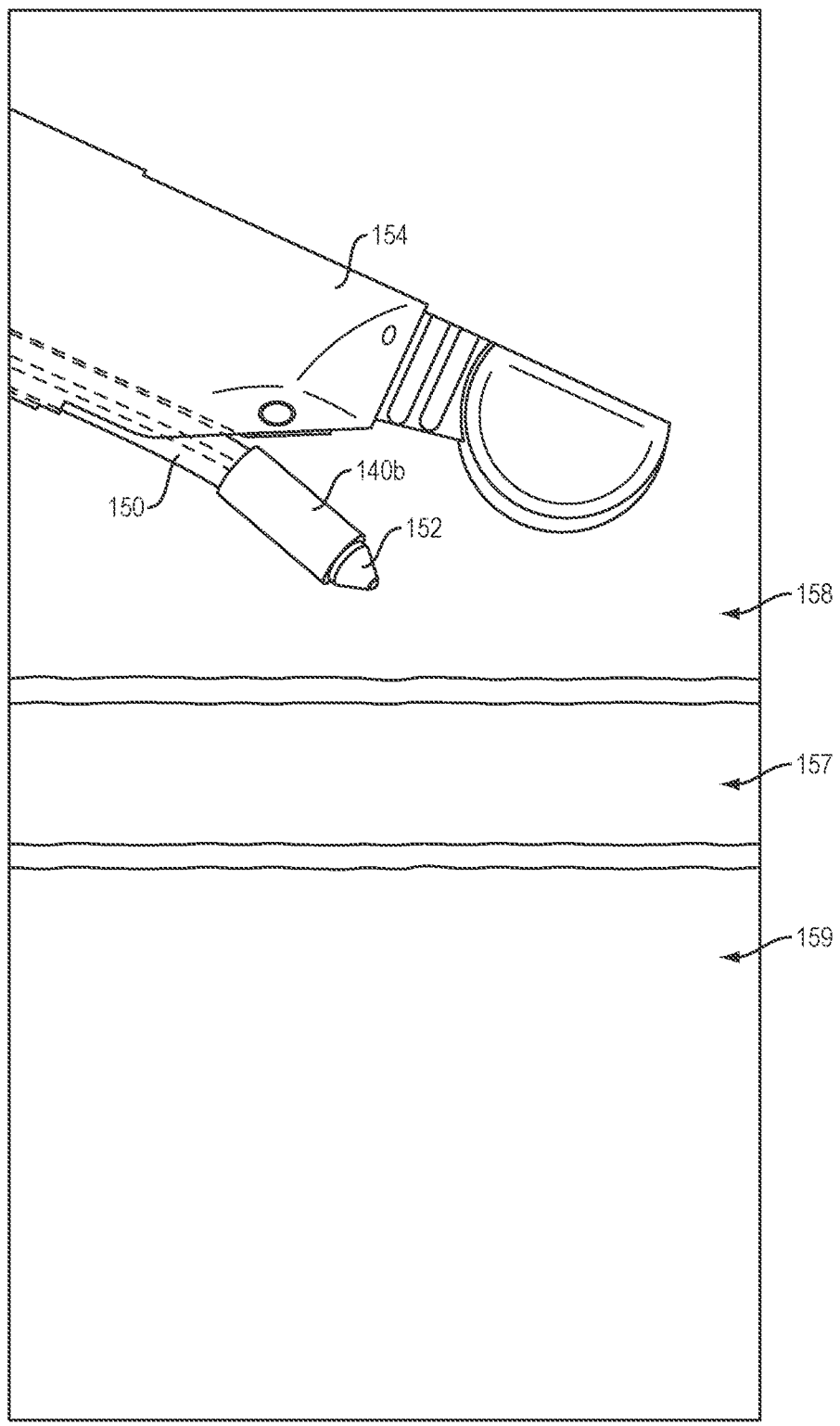
FIGS. 4A-4F illustrate the steps involved in deploying a medical device between first and second body lumens, according to one embodiment of the present disclosure.
Figure 4B:
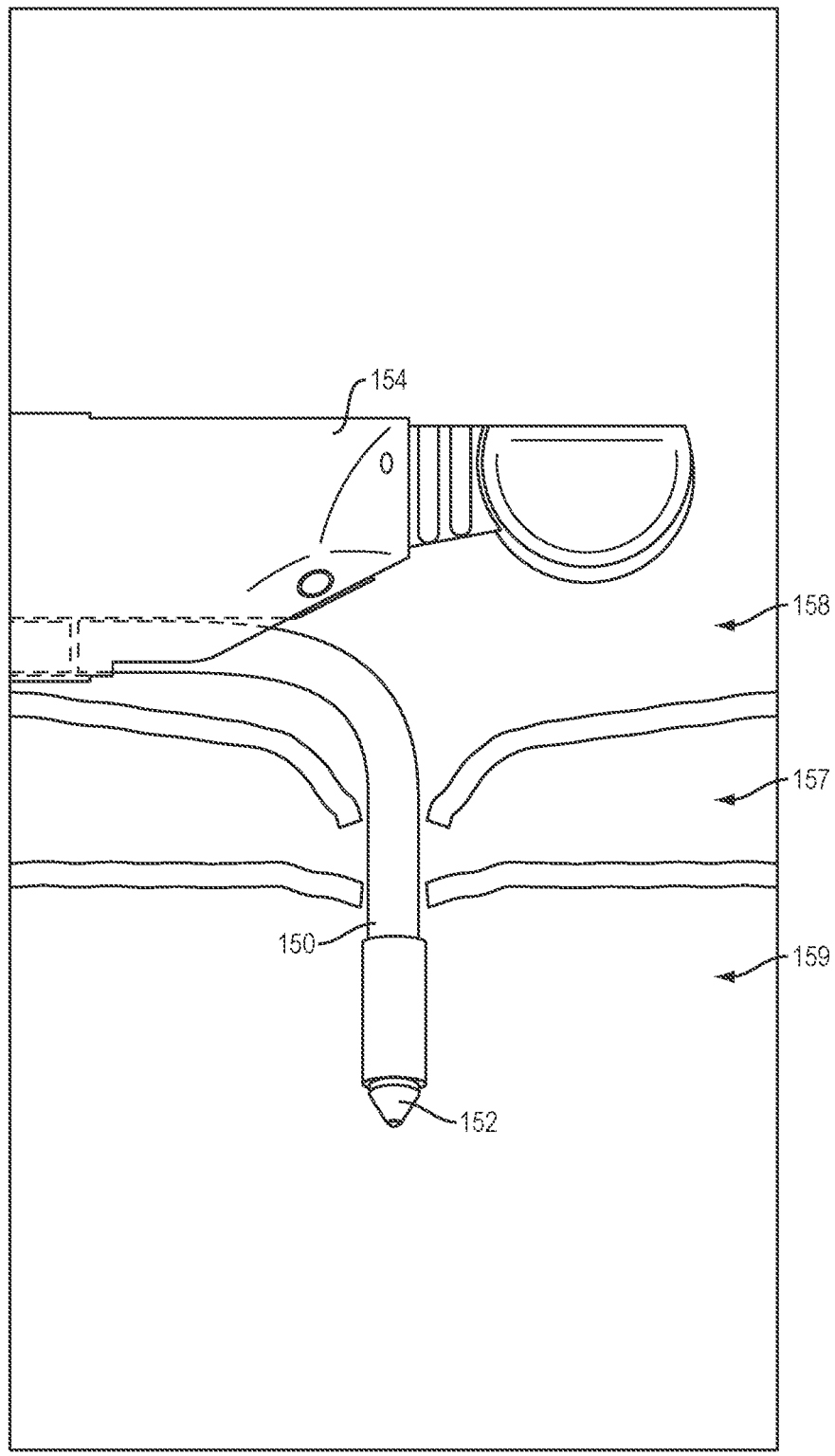

Referring to FIGS. 4A-4F, in use and by way of example, a delivery device 154 (e.g., endoscope, echoendoscope, duodenoscope, etc.) may be advanced into a first body lumen 158 such that a distal end of a delivery catheter 160 extending through a lumen of the delivery device 154 is positioned adjacent to a tissue wall of the first body lumen 158. A medical device (not shown) of the present disclosure may be disposed in the unexpanded configuration within the lumen of a delivery catheter 160, which may include a tissue-penetrating element 152 (FIG. 4A). A sharpened distal end of the tissue-penetrating element 152 may be advanced through the tissue wall of a first body lumen 158 (e.g., the stomach or duodenum) and through the tissue wall of a second body lumen 159 (e.g., the peritoneal cavity) (FIG. 4B). Additionally, or alternatively, the tissue penetrating element may comprise a conductive element (e.g., halo wire cone with proximally extending arms) that is configured to receive heat or energy (e.g., RF energy) for the purpose of creating openings.

In various embodiments, the tissue penetrating element 152 may be advanced over a guidewire (not shown) previously advanced through the first and second body lumens 158, 159 such that a distal end of the guidewire is disposed within the second body lumen 159. Alternatively, in the method above, a separate instrument with a sharpened distal tip may be advanced along the path above and into the second body lumen 159 to create a path. A guidewire (not shown) may be put in place, or left in place if used to guide the separate instrument, and the separate instrument withdrawn over the guidewire.

A medical device 100, 200, 300 according to the various embodiments described above, loaded on the delivery catheter 150, may be inserted over the guidewire, and the medical device then deployed according to the steps outlined below.

Figure 4C:
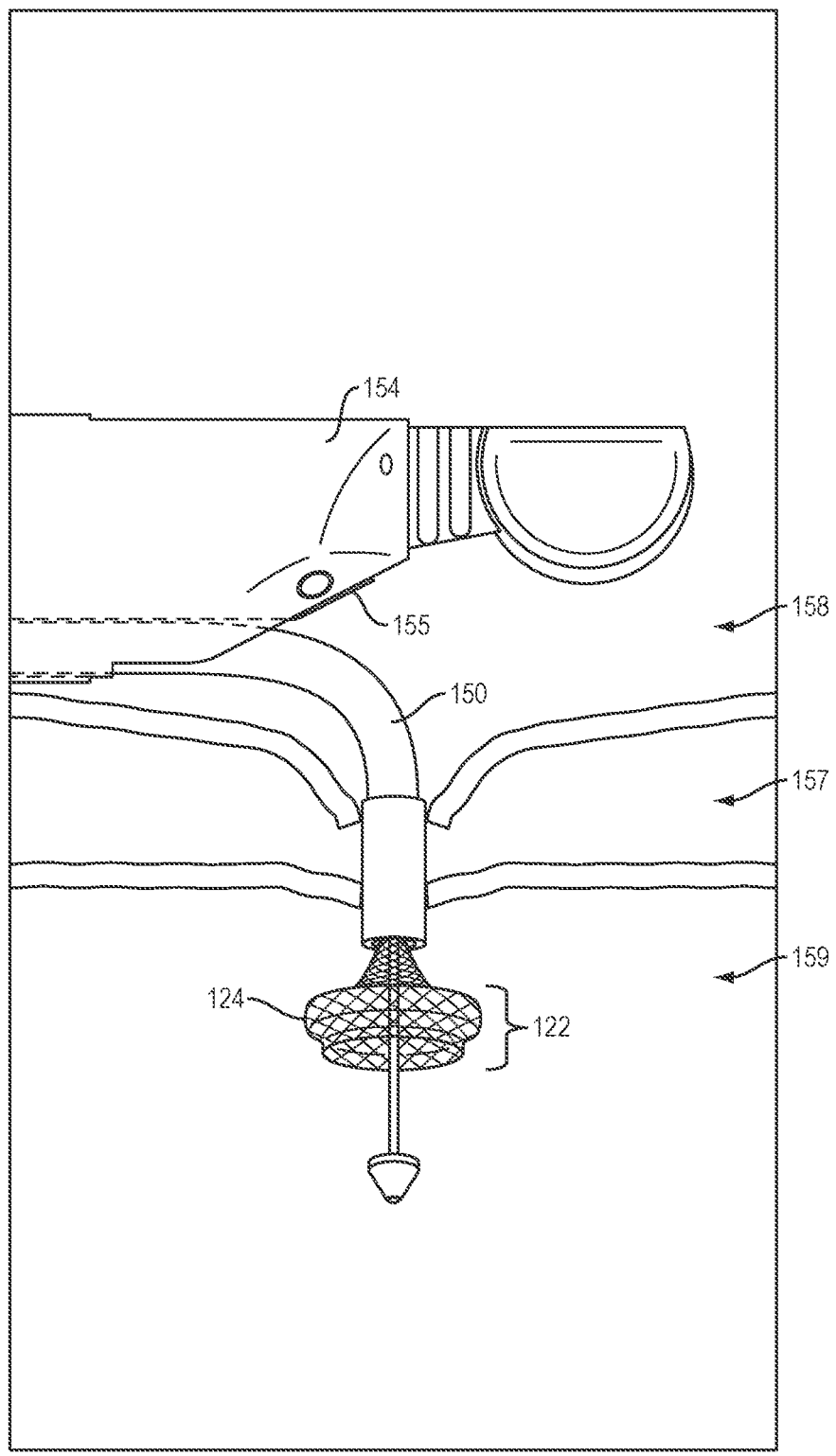

The distal portion 122 of the medical device 100, 200, may then be further advanced distally beyond the lumen of the delivery catheter 150 (which may or may not also include tissue-penetrating element 152), and/or an outer sheath of the delivery catheter 150 may be retracted proximally from the end of the medical device, such that the distal retention member 124 is fully deployed within the second body lumen 159 (FIG. 4C).

Figure 4D:
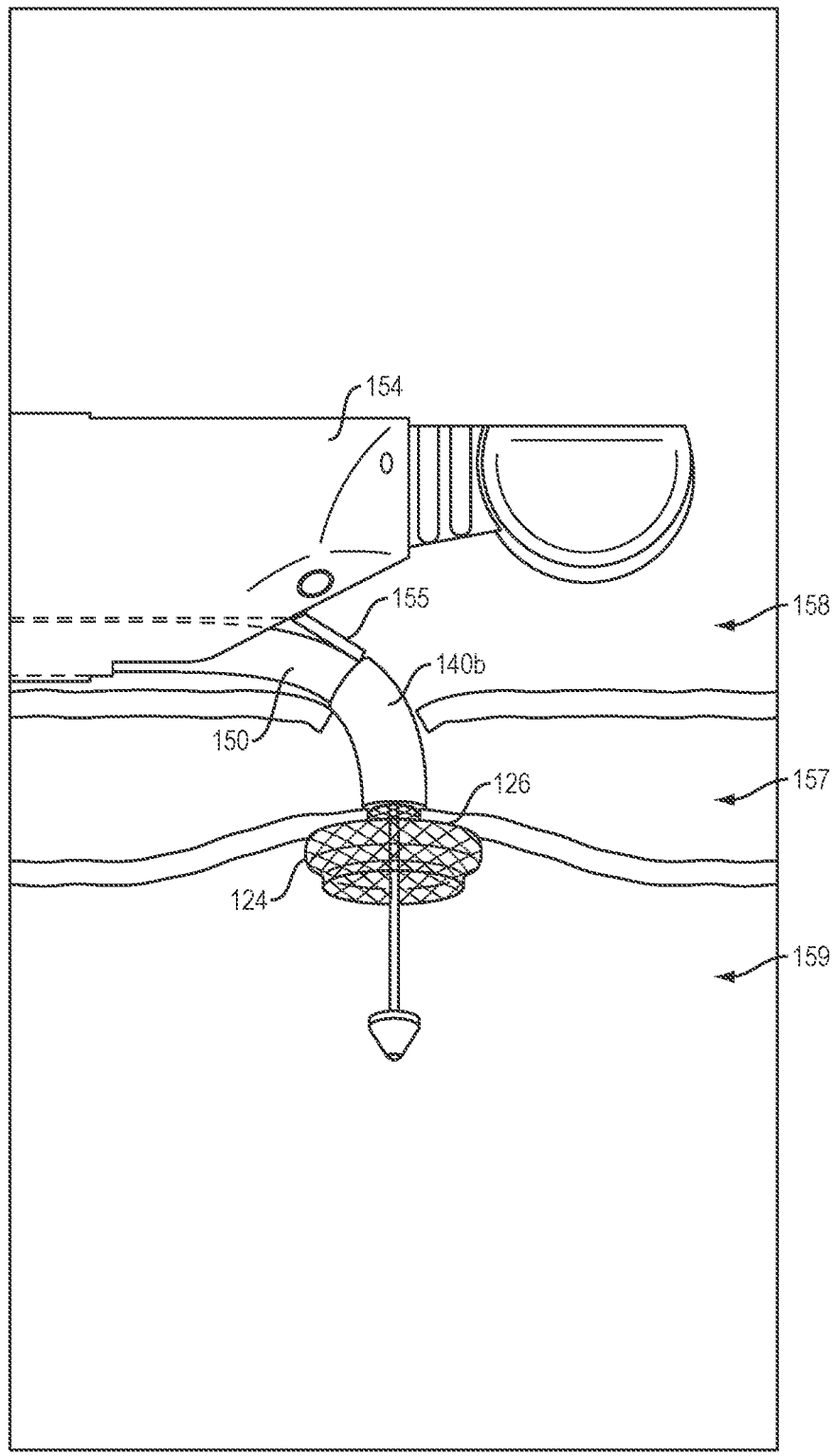
Figure 4E:
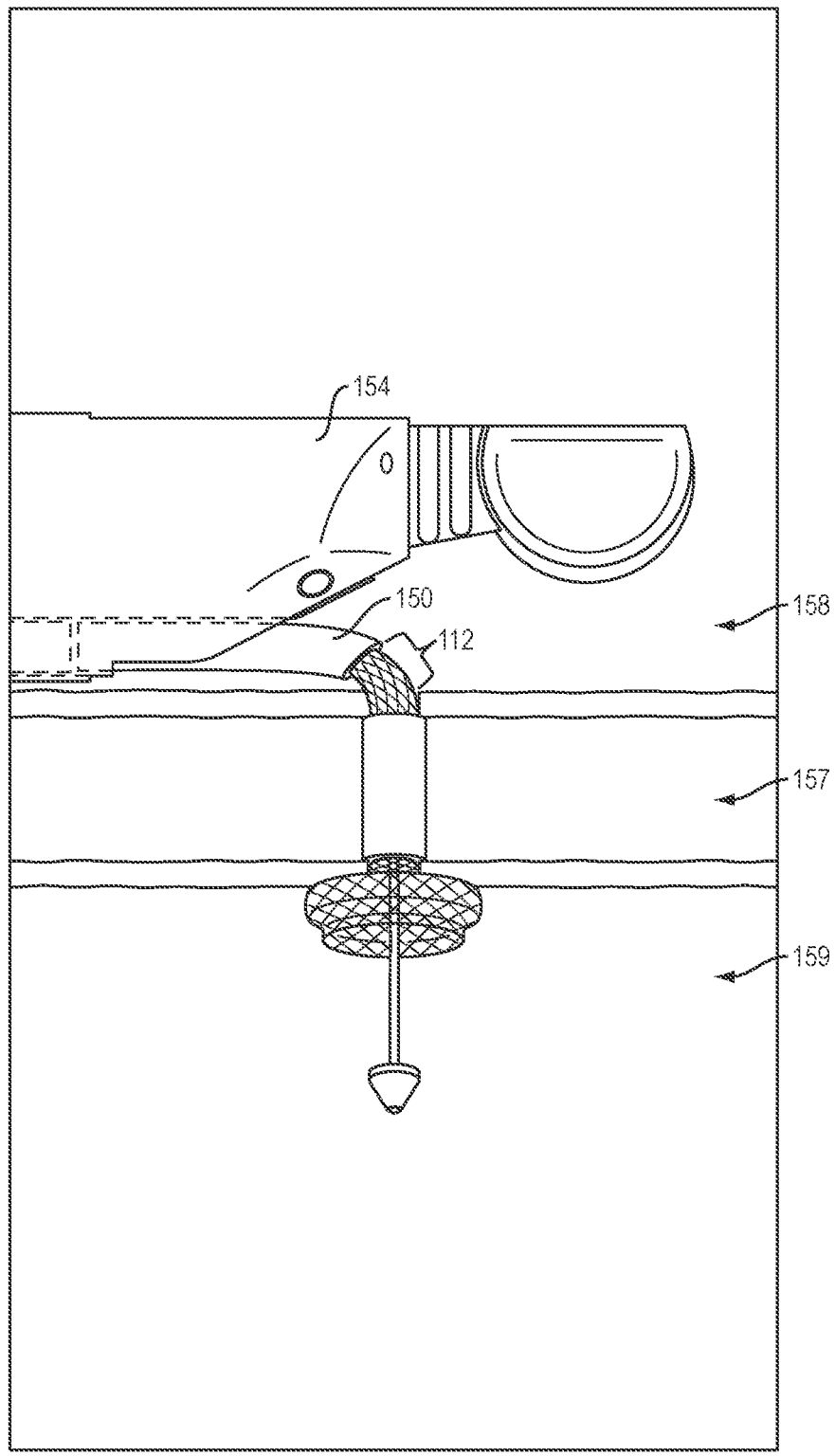

The delivery catheter 150 may then be retracted to place the surface 126 of the distal retention member 124 in contact with the inner surface of the tissue wall of the second body lumen 159 (FIG. 4D). In one embodiment, the flexible member 140b (e.g., of medical device 200) may be disposed around an outer surface of a distal portion of the delivery catheter 150. With the distal portion of the delivery catheter 150 disposed within the space 157 between the first and second body lumens 158, 159, the medical professional may raise the elevator 155 on the delivery device 154 such that a leading edge of the elevator engages a proximal end of the flexible member 140 (FIG. 4D). The medical professional may then further proximally retract the delivery catheter 150 to peel or roll the flexible member 140 off the delivery catheter 150 and onto/around the saddle region 130 and along a portion of all or a substantial portion of the length of the saddle region 130, e.g., extending in the space 157 between the first and second body lumens 158, 159 (FIG. 4E). Although not depicted, in various embodiments the flexible member 140a of medical devices 100 or 300 may be disposed around the outer surface of the distal portion of the delivery catheter and peeled/rolled off as described above.

In other embodiments, e.g., in which the flexible member 140a, 140b is permanently attached to, or integrally formed with, the elongate tubular body 110, the flexible member may be disposed around the elongate tubular body 110 within the lumen of the delivery catheter 150 such that the flexible member 140a, 140b and saddle region 130 are simultaneously deployed within the space 157 between the first and second body lumens 158, 159 as the delivery catheter 150 is retracted.

Figure 4F:
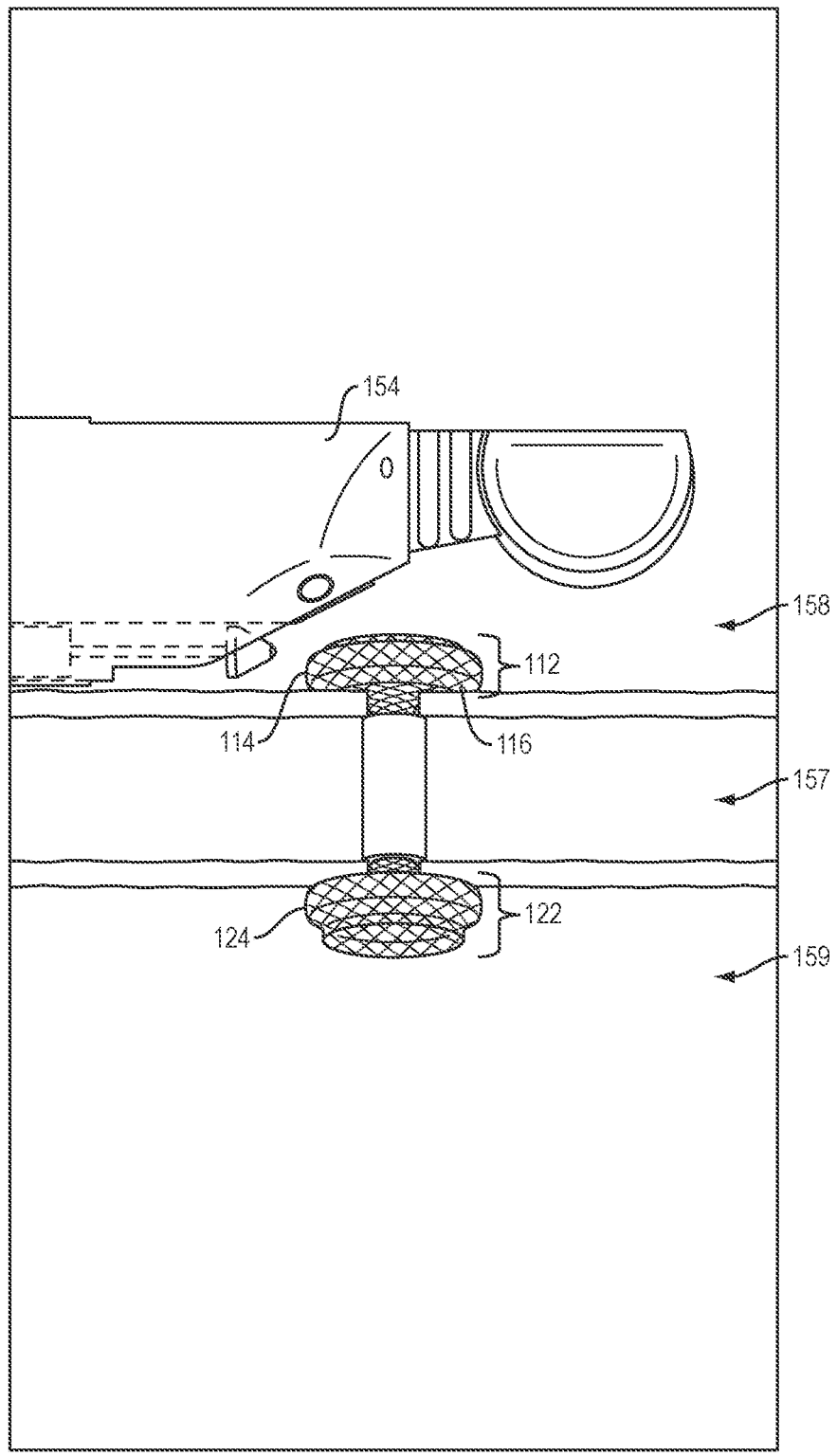

The delivery catheter 150 may then be further proximally retracted into the first body lumen 158, and the proximal portion of the medical device 100, 200, 300 advanced distally beyond the lumen of the delivery catheter 150, and/or the outer sheath of the delivery catheter 150 may be further retracted proximally from about the medical device, such that the proximal retention member 114 is fully deployed within the first body lumen 158 and the surface 116 of the proximal retention member 114 is placed in contact with the inner surface of the tissue wall of the first body lumen 158 (FIG. 4F).

In various embodiments, the compliant or semi-compliant materials comprising the flexible member 140a, 140b may be configured such that the lumen 141 may move (e.g., stretch) from the first or second inner dimension $d_1$, $d_2$ to a third inner dimension $d_3$ (not shown) greater than the respective first or second inner dimension $d_1$, $d_2$. For example, a separate medical device may be advanced into and through the saddle region 130 with a threshold level of force sufficient to extend through the constricted portion of the saddle region 130. In various embodiments, the flexible member 140a, 140b may constrict around and sealingly engage an outer surface of the separate medical device extending through the saddle region 130.

Referring to FIG. 5A, in one embodiment, a user may advance a medical tool 153a (e.g., drainage catheter, infusion catheter, micro-infusion catheter, etc.) through a previously implanted medical device 200, e.g., under endoscopic guidance, and with or without the aid of a previously placed guidewire for the medical tool. In response to a threshold level of force applied to the constricted portion of the saddle region 130 by the medical tool 153a, the lumen 141 of the flexible member may move from the first or second inner dimension $d_1$ or $d_2$, to the larger third inner dimension $d_3$, thereby allowing the medical tool 153a to extend into the second body lumen 159. In various embodiments, the medical tool 153a may deliver a therapeutic agent into a cavity or space surrounding or adjacent to a diseased tissue or organ. In addition to delivering an effective dose of the therapeutic agent directly within the target body lumen for maximum beneficial effect, the ability of the flexible member 140b and saddle region 130 of the medical device 200 to move between the closed and open configurations, may allow a prolonged regimen (e.g., weeks, months or years) of one or more therapeutic agents to be administered without causing undue discomfort to the patient. In addition, or alternatively, the medical tool 153a may be configured to lavage and/or suction fluid and/or debris from within an abscess or pseudocyst.

Referring to FIG. 5B, in another embodiment, a drainage device 153b (e.g., a plastic biliary stent, etc.) may be positioned within a previously implanted medical device 200, e.g., under endoscopic guidance to provide an open flow path therethrough. Once the medical tool (FIG. 5A) or drainage device (FIG. 5B) is proximally withdrawn from within the medical device 200, the lumen 141 of the flexible member 140b may return to the first or second inner dimension $d_1$, $d_2$ and saddle region 130 may return to the completely or partially closed position to limit and/or prevent flow therethrough.

Referring to FIGS. 6A-6C, in embodiments of the present disclosure in which the flexible member 140b is not permanently attached to, or integrally formed with, the elongate tubular body 110, a medical professional may remove or retrieve the flexible member 140b from its position around the saddle region 130, and along at least a portion of the length of the saddle region 130, such that the saddle region 130 moves to a fully non-constrained position. For example, using forceps or another suitable grasping tool, a medical professional may grasp an edge of the proximal retention member and draw the proximal retention member into the lumen of a delivery catheter (not shown), thereby returning (e.g., collapsing) the proximal retention member to the constrained position. A second medical tool 153, e.g., forceps, etc., may then be advanced through the lumen of the delivery catheter, or along an external surface of the delivery catheter, to grasp a proximal end of the flexible member 140b. While maintaining the location of the medical device 200, within the respective first and second body lumens 158, 159, the medical professional may proximally retract and remove the flexible member 140b from the elongate tubular body 110 of the medical device 200. The non-constrained medical device may then allow unrestricted flow and/or access through the saddle region.

It should be appreciated that FIGS. 5A-5B and 6A-6B are provided for illustration purposes only, and are in no way limited to medical device 200, but may include either of medical devices 100, 300. The elongate tubular body 110 of any of the medical devices 100, 200, 300 depicted in FIGS. 1A-3C may be formed of one or more braided filaments (e.g., nitinol wire, etc.). The proximal retention member 114, distal retention member 124 and/or saddle region 130 may further include a membrane, covering or coating on an inner and/or outer surface thereof to define a contiguous open interior passage configured for controlled flow (e.g., body fluids, materials, and the like) and/or access therethrough. The coating may comprise a variety of non-degradable and biocompatible polymeric materials (e.g., upon exposure to bodily fluids such as bile), including, for example, silicones, rubbers, polyethylenes, PVDF, Chronoflex® and thermoplastic elastomers, such that the coating conforms to the medical device in the unexpanded and expanded configurations.

Although the flexible member(s) 140a, 140b of the present disclosure are depicted as substantially circular, in various embodiments, the flexible member(s), e.g., rings/collars 140a or sheaths/tubes 140b, may include a variety of sizes, shapes, configurations and/or thicknesses. As will be understood by those of skill in the art, the constrictive force applied by the flexible members may be determined based on the size, shape, thickness, durometer value and/or composition of the materials which comprise the flexible member(s). In addition, or alternatively, in various embodiments a flexible sheath 140b of the present disclosure may include an inner/interior portion which is thinner, weaker and/or more flexible than the surrounding outer/end portions, thereby providing a reservoir, e.g., for a therapeutic agent (as discussed above).

The proximal and distal retention members 114, 124 of any of the medical devices 100, 200, 300 depicted in FIGS. 1A-3C may include various configurations, such that one or more of the retention members extend radially at an angle from the longitudinal axis of the elongate tubular body that is not necessarily perpendicular to the elongate tubular body and/or the surfaces are not necessarily planar. In various embodiments, the angle of the retention members relative to the circumference and longitudinal axis of the elongate tubular body may assume other degrees (e.g., 30, 45, 60, 75 degrees, etc.) or may change degrees along the length of the retention members creating inflection points in the retention members. For example, one or both of the proximal and distal retention members may extend outward towards an end of the elongate tubular body, back towards a center portion of the elongate tubular body, or change directions in some combination of both.

For example, one or both of the proximal and distal retention members may flare away from a longitudinal axis of the saddle region into flange configurations on opposite ends of the saddle region when in the expanded configuration. Each flange configuration may include at least first and second points of inflection that may define first and second segments of the flange. The first segment may extend from the first inflection point toward a center plane perpendicular to the longitudinal axis of the tubular body, and the second segment may extend from the first inflection point away from the center plane. An angle of the first inflection point defined by the first segment and the saddle region may be at least as great as an opposing angle of the second inflection point defined by the first segment and the second segment.

As another example, each flange may include at least first and second points of inflection that define first and second segments of the flange, wherein the second points of inflection may be further spaced radially from the longitudinal axis than the first points of inflection, and the second points of inflection may be closer than the first points of inflection to a center plane along the longitudinal axis. The flanges on opposite ends of the saddle region may touch planes that are parallel to the longitudinal axis, at least one plane each above and below the longitudinal axis, at at least two separate points along the parallel planes.

As yet a further example, each flange configuration may include at least first and second points of inflection that define first and second segments of the flange. The first segment may extend from the first inflection point toward a center plane perpendicular to the longitudinal axis of the tubular body, and the second segment may extend from the second inflection point away from the center plane. The intersection of the saddle region and the first segments may define the first inflection points, and the intersection of the first segments and second segments may define second inflection points. An angle of the first inflection points may be 90 degrees or less, and an opposing angle of the second inflection points may be 90 degrees or less.

In various embodiments, one or both of the proximal and distal retention members may include an outer diameter $d_1$ that is greater than an outer diameter $d_2$ of the saddle region. For example, outer diameter $d_1$ may be as much as 75%-100% greater than an outer diameter $d_2$ of the saddle region. By way of non-limiting example, outer diameter $d_1$ may be approximately 7.0 mm to approximately 30 mm, and outer diameter $d_2$ may be approximately 3.0 mm to approximately 15.0 mm. In various embodiments, the size (e.g., diameter) of the opening formed between the first and second body lumens may be increased or decreased by increasing or decreasing the size (e.g., width) of the proximal and distal retention members (e.g., increasing or decreasing the surface area of the tissue layers compressed between the proximal and distal retention members). In addition, or alternatively, a length of the elongate tubular body in the expanded configuration may be foreshortened, e.g., at least 40% shorter than a length of the elongate tubular body when in the unexpanded configuration.

Various embodiments, e.g., the medical devices 100, 200, 300 of the present disclosure, may include a double-walled flange as the proximal and distal retention members at either end of the elongate tubular body in the expanded configuration. In various other embodiments, the proximal and/or distal retention members may include a variety of other configurations, including, but not limited to single-walled flange structures at either end, and/or more than one single-walled or double-walled flange structure at either end. The walls of the flanges above and/or below the longitudinal axis may be symmetrical or may be asymmetrical. The walls of the flanges above and/or below the longitudinal axis may have multiple inflection points, as mentioned above, that define segments of the walls of the flange that change direction as the walls extend radially away from the longitudinal axis (e.g., segments can extend radially parallel to, away from and/or toward, a radial center line of the body). The segments may extend along a straight line or may be curved, or may include a combination of straight lines and curves.

In various embodiments, any of the woven, braided and/or knitted filaments, which comprise the elongate tubular body may include a variety of different cross-sectional shapes (e.g., oval, round, flat, square, etc.) and may be formed from metals and/or polymers, including shape memory metals and polymers. The woven, braided and/or knitted filament may further include a single filament woven upon itself, or multiple filaments woven together.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
an elongate tubular body comprising a proximal portion, a distal portion, and a length therebetween, the elongate tubular body defining a lumen along the length;
the elongate tubular body having an unexpanded configuration, and an expanded configuration wherein the proximal portion expands into a proximal retention member and the distal portion expands into a distal retention member leaving a length of a saddle region extending therebetween; and
two flexible collars disposed around the saddle region along separate portions of the length of the saddle region;
wherein each of the flexible collars is configured to constrict at least a portion of the saddle region to define a fluid reservoir between the flexible collars, and to allow controlled flow of fluid from the reservoir to be delivered through a lumen defined by at least one of the collars.

2. The medical device of claim 1, wherein each flexible collar defines a lumen, wherein each flexible collar is configured to move from a non-expanded configuration to an expanded configuration, and wherein an inner dimension of the lumen of each flexible collar in the non-expanded configuration is less than an inner dimension of the lumen of each flexible collar in the expanded configuration.

3. The medical device of claim 2, wherein the lumens defined by the flexible collars are completely closed when the flexible collars are in the non-expanded configuration to retain fluid within the reservoir.

4. The medical device of claim 2, wherein the lumen of the constricted portion of the length of the saddle region is partially closed when the flexible collars are in the non-expanded configuration.

5. The medical device of claim 1, wherein the device further comprises a therapeutic agent disposed within the reservoir and flowable from the reservoir through the proximal retention member.

6. The medical device of claim 1, wherein the device further comprises a therapeutic agent disposed within the reservoir and flowable from the reservoir through the distal retention member.

7. The medical device of claim 1, wherein a surface of the proximal retention member is configured to contact an inner surface of a tissue wall of a first body lumen, and a surface of the distal retention member is configured to contact an inner surface of a tissue wall of a second body lumen.

8. The medical device of claim 1, wherein the flexible collars and the constricted portion of the length of the saddle region are configured to move from a first diameter configuration to a second diameter configuration in response to a threshold level of force to allow controlled flow of a fluid from within the reservoir through at least one of the flexible collars.

* * * * *